United States Patent
Tabuteau

(10) Patent No.: US 8,901,162 B1
(45) Date of Patent: *Dec. 2, 2014

(54) SUBSTITUTED IMIDAZOLIUM COMPOUNDS FOR TREATING DISEASE

(71) Applicant: Antecip Bioventures II LLC, New York, NY (US)

(72) Inventor: Herriot Tabuteau, New York, NY (US)

(73) Assignee: Antecip Bioventures II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/288,713

(22) Filed: May 28, 2014

Related U.S. Application Data

(60) Provisional application No. 61/933,608, filed on Jan. 30, 2014.

(51) Int. Cl.
| | |
|---|---|
| *C07D 233/60* | (2006.01) |
| *A61K 31/4172* | (2006.01) |
| *C07D 233/64* | (2006.01) |
| *C07F 9/38* | (2006.01) |

(52) U.S. Cl.
CPC ............ *C07F 9/3873* (2013.01); *C07D 233/64* (2013.01)
USPC ...... 514/399; 548/112; 548/341.5; 548/342.1

(58) Field of Classification Search
CPC .......................... C07D 233/60; A61K 31/4172
USPC ..................... 548/112, 341.5, 342.1; 514/399
See application file for complete search history.

(56) References Cited

FOREIGN PATENT DOCUMENTS

EP        2192126 B1      3/2013

OTHER PUBLICATIONS

U.S. Appl. No. 14/288,241, filed May 2014, Tabuteau, H.*
U.S. Appl. No. 14/288,720, filed May 2014, Tabuteau, et al.*

* cited by examiner

*Primary Examiner* — Michael Barker
(74) *Attorney, Agent, or Firm* — K&L Gates LLP; Louis C. Cullman; Brent A. Johnson

(57) ABSTRACT

The present disclosure relates to therapeutic compositions comprising substituted imidazoliums having multiple acidic groups. The compounds may be used to treat diseases or conditions such as those associated with bone, cancer, or pain. Compositions, dosage forms, methods of treating diseases or conditions, methods of preparation, and other related embodiments related to the substituted imidazoliums are also described herein.

18 Claims, No Drawings

SUBSTITUTED IMIDAZOLIUM COMPOUNDS FOR TREATING DISEASE

CROSS-REFERENCE

This application claims the benefit of U.S. Provisional Application No. 61/933,608, filed Jan. 30, 2014, which is incorporated by reference herein in its entirety.

FIELD

Some embodiments relate to therapeutic compositions comprising substituted imidazoliums having multiple acidic groups.

BACKGROUND

Substituted imidazoles have been shown to have many medical uses. For example, many drugs contain an imidazole ring, such as antifungal drugs, nitroimidazole, and the sedative midazolam. However, imidizolium compounds having therapeutic activity are much less common.

SUMMARY

Compounds according to a formula:

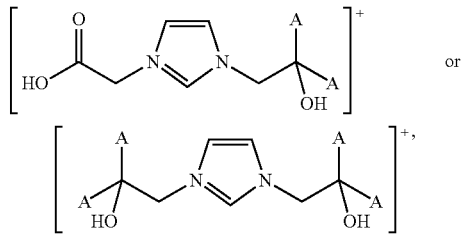

or a salt thereof; wherein each A is independently an acidic functional group, and wherein the imidazoliumyl rings may optionally contain additional substituents, may be used for a number of medical purposes, such as treatment of undesirable conditions or diseases, including disease or conditions related to bone, cancer, and/or pain. In some embodiments, each A is $CO_2H$, $SO_3H$, $OSO_2$, or $PO_3H_2$.

DETAILED DESCRIPTION

Optionally substituted Compounds 1 and 2 can be used to treat diseases typically treated by bisphosphonates.

Compound 1

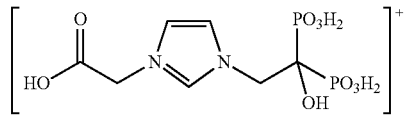

Compound 2

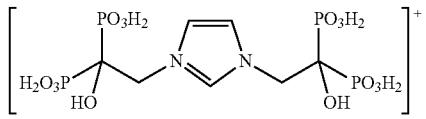

Some embodiments include optionally substituted Compound 1 or optionally substituted Compound 2, such as Compound 1 or Compound 2 optionally having substituents on the imidazolium moiety.

Some embodiments include a composition comprising optionally substituted Compound 1 or optionally substituted Compound 2.

Some embodiments include a dosage form comprising optionally substituted Compound 1 or optionally substituted Compound 2.

Some embodiments include a method of treating a disease or condition related to bone, cancer, or pain, comprising administering a dosage form comprising optionally substituted Compound 1 or optionally substituted Compound 2 to a mammal in need thereof.

In some embodiments, a dosage form of optionally substituted Compound 1 or optionally substituted Compound 2, such as an oral dosage form, can be used to treat or alleviate pain or related conditions.

Some embodiments include a method of relieving pain associated with an arthritis comprising administering an oral dosage form containing optionally substituted Compound 1 and/or optionally substituted Compound 2 to a human being in need thereof.

Some embodiments include a method of treating complex regional pain syndrome comprising administering an oral dosage form containing optionally substituted Compound 1 and/or optionally substituted Compound 2 to a mammal in need thereof.

Some embodiments include a method of relieving inflammatory pain comprising administering an oral dosage form containing optionally substituted Compound 1 and/or optionally substituted Compound 2 to a mammal in need thereof.

Optionally substituted Compound 1, or a salt thereof, or optionally substituted Compound 2, or a salt thereof, (referred to hereafter as "subject compounds") may be used for a number of medical purposes, such as treatment of undesirable conditions or diseases, including pain relief. This may be accomplished in many instances by administration of oral dosage forms. Generally, an oral dosage form comprising a subject compound is administered parenterally or orally to a mammal, such as a human being, at least once, to treat a disease or condition, or to relieve pain.

The term "treating" or "treatment" broadly includes any kind of treatment activity, including the diagnosis, cure, mitigation, or prevention of disease in man or other animals, or any activity that otherwise affects the structure or any function of the body of man or other animals.

A subject compound may be used to treat, or provide relief of, any type of pain including, but not limited to, inflammatory pain, arthritis pain, complex regional pain syndrome, lumbosacral pain, musculoskeletal pain, neuropathic pain, chronic pain, cancer-related pain, acute pain, postoperative pain, etc. In some embodiments, pain relief may be palliative, or pain relief may be provided independent of improvement of the disease or condition or the underlying cause of the disease or condition. For example, although the underlying disease may not improve, or may continue to progress, an individual suffering from the disease may experience pain relief.

For example, a subject compound may be administered parenterally or orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, a subject compound may also be administered parenterally or orally to relieve neuropathic pain, including diabetic peripheral neuropathy, post-herpetic neuralgia, trigeminal neuralgia, monoradiculopathies, phantom limb pain, and central pain. Other causes of neuropathic pain include cancer-related pain, lumbar nerve root compression, spinal cord injury, post-stroke pain, central multiple sclerosis pain, HIV-associated neuropathy, and radio-therapy or chemo-therapy associated neuropathy.

In some embodiments, a subject compound may be administered parenterally or orally to relieve inflammatory pain including musculoskeletal pain, arthritis pain, and complex regional pain syndrome.

Examples of musculoskeletal pain include low back pain; and pain associated with vertebral crush fractures, fibrous dysplasia, osteogenesis imperfecta, Paget's disease of bone, transient osteoporosis, and transient osteoporosis of the hip.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropaties including Charcot's foot, axial spondyloarthritis including ankylosing spondylitis, and SAPHO syndrome.

In some embodiments, a human being that is treated for arthritis by a subject compound has an age of about 10 years to about 90 years, about 20 years to about 80 years, about 30 years to about 75 years old, about 40 years to about 70 years, about 1 year to about 16 years, or about 80 years to about 95 years.

In some embodiments, a human being that is treated for arthritis by a subject compound has suffered from the arthritis for at least 1 month, at least 2 months, at least 6 months, or at least 1 year.

In some embodiments, the arthritis affects, a knee, an elbow, a wrist, a shoulder, or a hip.

In some embodiments, a subject compound may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component.

Complex regional pain syndrome is a debilitating pain syndrome. It is characterized by severe pain in a limb accompanied by edema, and autonomic, motor and sensory changes.

In some embodiments, a subject compound may be administered to treat a condition such as osteoporosis, rheumatoid arthritis, bone fracture, excessive bone resorption, systemic lupus erythematosus (SLE), cancer, tumor induced hypocalcemia, bone metastasis, prostate cancer, metastatic bone cancer, lung cancer, multiple myeloma, breast cancer and any solid tumor that induces metastatic disease.

A subject compound may also be administered parenterally or orally to relieve cancer-related pain, including pain associated with multiple myeloma and bone metastases from solid tumors. In some embodiments, a subject compound is used to treat pain that is not cancer-related pain. For example, a subject compound may be used to treat pain that is not associated with multiple myeloma, bone metastasis from solid tumors, hypercalcemia of malignancy, giant cell tumor of bone, blood cancers or leukemias, or solid tumors or cancers. In some embodiments, enhanced bioavailability of the a subject compound may be achieved in treating one of these conditions by administering a dosage form comprising a subject compound in the form of a disodium salt. This may allow a reduced molar amount of the disodium salt to be used as compared to what would be used with the diacid form.

In addition to relieving pain, a subject compound may also be useful to treat diseases or conditions that may or may not include a pain component. For example, a subject compound may be useful to treat any of the pain conditions or types of conditions listed above, including treatment that does not simply relieve the pain of those conditions, and treatment that is carried out in such a way that the condition is treated without pain relief occurring. In addition to any pain relief a subject compound may or may not provide, a subject compound may be used to treat a disease or condition such as a metabolic disease or condition; an inflammatory disease or condition, including an inflammatory disease or condition that is not associated with pain; a cancer disease or condition; a neurological disease or condition; etc.

In some embodiments, subject compound may also be useful to treat complex regional pain syndrome, rheumatoid arthritis, osteoarthritis, erosive osteoarthritis, axial spondyloarthritis including ankylosing spondylitis, acute vertebral crush fracture, fibrous dysplasia, SAPHO syndrome, osteoporosis, transient osteoporosis, or transient osteoporosis of the hip.

In some embodiments, oral administration of a subject compound may also be useful to treat hypercalcemia of malignancy, multiple myeloma, bone metastases from solid tumors, Paget's disease of bone, giant cell tumor of bone, blood cancers or leukemias, or solid tumors or cancers.

Unless otherwise indicated, when a compound or chemical structural feature, such an imidazoliumyl ring, is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that occupies a position normally occupied by one or more hydrogen atoms attached to an unsubstituted parent compound or structural feature. In some embodiments, a substituent may be an ordinary organic moiety known in the art, which may have a molecular weight (e.g. the sum of the atomic masses of the atoms of the substituent) of 15 g/mol to 50 g/mol, 15 g/mol to 100 g/mol, 15 g/mol to 150 g/mol, 15 g/mol to 200 g/mol, 15 g/mol to 300 g/mol, or 15 g/mol to 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, 0, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

Unless otherwise indicated, any reference to a compound herein, such as a subject compound, by structure, name, or any other means, includes pharmaceutically acceptable salts, such as the disodium salt; alternate solid forms, such as polymorphs, solvates, hydrates, etc.; tautomers; or any other chemical species that may rapidly convert to a compound described herein under conditions in which the compounds are used as described herein.

Examples of salts of Compound 1 are shown below:

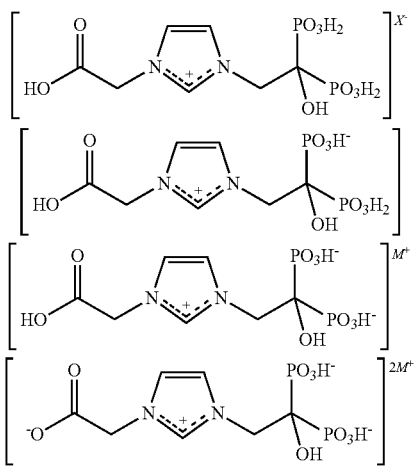

wherein $X^-$ is any suitable anion, e.g. $F^-$, $Br^-$, $Cl^-$, $I^-$, acetate, etc.; and $M^+$ is any suitable cation, e.g. $Na^+$, $K^+$, $NH_4^+$, etc. Many other salt forms are also possible.

In some embodiments, Compound 1 is administered in a dosage form comprising a salt form, such as a zwitterionic form, or a salt of a cation, a monoanion, a dianion, a trianion, etc., of Compound 1.

Examples of salts of Compound 2 are shown below:

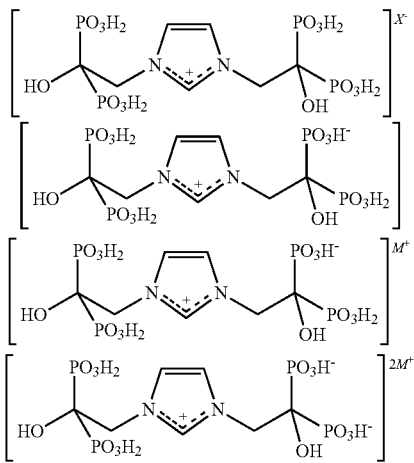

wherein $X^-$ is any suitable anion, e.g. $F^-$, $Br^-$, $Cl^-$, $I^-$, acetate, etc.; and $M^+$ is any suitable cation, e.g. $Na^+$, $K^+$, $NH_4^+$, etc. Many other salt forms are also possible.

In some embodiments, Compound 2 is administered in a dosage form comprising a salt form, such as a zwitterionic form, or a salt of a cation, a monoanion, a dianion, a trianion, etc., of Compound 2.

Some embodiments include a pharmaceutical dosage form comprising a subject compound. A subject compound may be the sole active agent present in the dosage form, or may be combined with other active agents. For example, a subject compound may be at least 0.5% w/w, at least 1% w/w, at least 5% w/w, at least 10% w/w, at least 20% w/w, at least 50% w/w, at least 80% w/w, at least 90% w/w, or at least 95% w/w, of the total amount of therapeutically active agent present in the pharmaceutical dosage form.

A subject compound may be combined with zoledronic acid in a dosage form. Alternatively, zoledronic acid may be less than 10%, less than 50%, less than 75%, or less than 95% w/w of the total amount of therapeutically active agent present in the pharmaceutical dosage form.

Some embodiments include a dosage form comprising zoledronic acid and a subject compound. In some embodiments, the subject compound is about 0.1% w/w or less of the total amount of zoledronic acid and subject compound. In some embodiments, a dosage form comprises zoledronic acid and Compound 1, wherein Compound 1 is 0.1% w/w or less of the total amount of zoledronic acid and Compound 1. In some embodiments, a dosage form comprises zoledronic acid and Compound 2, wherein Compound 2 is 0.1% w/w or less of the total amount of zoledronic acid and Compound 2.

In some embodiments a subject compound, is the sole active agent present in the pharmaceutical dosage form.

Some embodiments include a composition comprising more than 1% w/w, more than 10% w/w, more than 20% w/w, more than 50% w/w, more than 70% w/w, or more than 90% w/w, of a subject compound.

Some embodiments include a method of preparing a dosage form for use in treating a disease or condition associated with bone, cancer, or pain, comprising combining a subject compound with a pharmaceutically acceptable excipient, or enclosing a subject compound in a capsule or coating.

A subject compound may be combined with a pharmaceutical carrier or excipient selected on the basis of the chosen route of administration and standard pharmaceutical practice as described, for example, in Remington's Pharmaceutical Sciences, 2005, the disclosure of which is hereby incorporated herein by reference, in its entirety. The relative proportions of active ingredient and carrier may be determined, for example, by the solubility and chemical nature of the compounds, chosen route of administration and standard pharmaceutical practice.

A subject compound may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

A subject compound may be administered to a human patient in a variety of forms adapted to the chosen route of administration, e.g., orally, rectally, or parenterally. Parenteral administration in this respect includes, but is not limited to, administration by the following routes: pulmonary, intrathecal, intravenous, intramuscular, subcutaneous, intraocular, intrasynovial, intraarticular, transepithelial including transdermal, sublingual and buccal; topically; nasal inhalation via insufflation; and rectal systemic.

The effective amount of a subject compound will vary depending on various factors known to the treating physicians, such as the severity of the condition to be treated, route of administration, formulation and dosage forms, physical characteristics of the bisphosphonate compound used, and age, weight and response of the individual patients. Some solid or liquid oral dosage forms may contain about 1 mg to about 1,000 mg of a subject compound.

A subject compound may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, coated tablets, troches, capsules, elixirs, dispersions, suspensions, solutions, syrups, wafers, patches, and the like.

Tablets, troches, pills, capsules and the like may also contain one or more of the following: a binder such as gum tragacanth, acacia, corn starch or gelatin; an excipient, such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the unit dosage form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially non toxic in the amounts employed.

The following embodiments are specifically contemplated:

Embodiment 1

A compound represented by a formula:

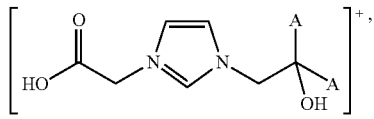

or a salt thereof;
wherein each A is independently an acidic functional group.

Embodiment 2

A compound represented by a formula:

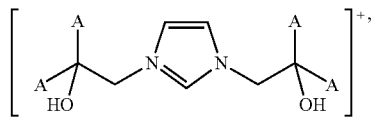

or a salt thereof;
wherein each A is independently an acidic functional group.

Embodiment 3

The compound of embodiment 1 or 2, wherein each A is $CO_2H$.

Embodiment 4

The compound of embodiment 1 or 2, wherein each A is $SO_2H$.

Embodiment 5

A compound represented by a formula:

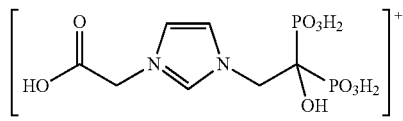

(Compound 1), or
a salt thereof.

Embodiment 6

A compound represented by a formula:

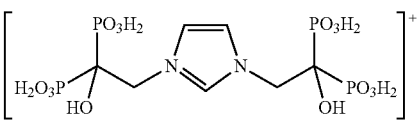

(Compound 2), or a salt thereof.

Embodiment 7

A pharmaceutical dosage form comprising a therapeutically effective amount of a compound of embodiment 1, 2, 3, 4, 5, or 6.

Embodiment 8

The pharmaceutical dosage form of embodiment 7, wherein Compound 1, or a salt thereof, is at least 0.5% w/w of the total amount of therapeutically active agent present in the pharmaceutical dosage form.

Embodiment 9

The pharmaceutical dosage form of embodiment 7 or 8, wherein Compound 2, or a salt thereof, is at least 0.5% w/w of the total amount of therapeutically active agent present in the pharmaceutical dosage form.

Embodiment 10

The pharmaceutical dosage form of embodiment 7, 8, or 9, further comprising zoledronic acid.

Embodiment 11

The pharmaceutical dosage form of embodiment 7, 8, or 9, wherein zoledronic acid is less than 95% w/w of the total amount of therapeutically active agent present in the pharmaceutical dosage form

Embodiment 12

The pharmaceutical dosage form of embodiment 7, wherein Compound 1, or a salt thereof, is the sole active agent present in the pharmaceutical dosage form.

Embodiment 13

The pharmaceutical dosage form of embodiment 7, wherein Compound 2, or a salt thereof, is the sole active agent present in the pharmaceutical dosage form.

Embodiment 14

A composition comprising more than 1% w/w of Compound 1.

Embodiment 15

A composition comprising more than 1% w/w of Compound 2.

Embodiment 16

A method of treating a disease or condition associated with bone, cancer, or pain, comprising administering a pharmaceutical dosage form of embodiment 7, 8, 9, 10, 11, 12, or 13 to a mammal in need thereof.

Embodiment 17

The method of embodiment 16, wherein the mammal is a human being.

Embodiment 18

The method of embodiment 16 or 17, wherein the disease or condition comprises an inflammatory pain, osteoporosis, or multiple myeloma.

Embodiment 19

A method of preparing a dosage form for use in treating a disease or condition associated with bone, cancer, or pain, comprising combining a therapeutically effective amount of a compound of embodiment 1, 2, 3, 4, 5, or 6 with a pharmaceutically acceptable excipient, or enclosing a therapeutically effective amount of a compound of embodiment 1, 2, 3, 4, 5, or 6 in a capsule or coating.

Embodiment 20

The method of embodiment 16, 17, or 19, wherein the disease of condition comprises acute pain, central pain, radiotherapy or chemo-therapy associated neuropathy, ankylosing spondylitis, arthritis, axial spondyloarthritis, blood cancers, bone fracture, bone metastases from solid tumors, bone metastasis, breast cancer, cancer, central multiple sclerosis pain, Charcot's foot, chronic pain, complex regional pain syndrome, diabetic peripheral neuropathy, erosive osteoarthritis, excessive bone resorption, fibrous dysplasia, giant cell tumor of bone, HIV-associated neuropathy, hypercalcemia of malignancy, inflammatory pain, juvenile rheumatoid arthritis, leukemias, low back pain, lumbar nerve root compression, lumbosacral pain, lung cancer, metastatic bone cancer, monoradiculopathies, multiple myeloma, musculoskeletal pain, neuropathic arthropaties, neuropathic pain, non-articular rheumatism, osteoarthritis, osteogenesis imperfecta, osteoporosis, Paget's disease, Paget's disease of bone, periarticular disorders, phantom limb pain, post-herpetic neuralgia, postoperative pain, post-stroke pain, prostate cancer, rheumatoid arthritis, SAPHO syndrome, sero-negative (non-rheumatoid) arthropathies, solid tumors or cancers, spinal cord injury, systemic lupus erythematosus, transient osteoarthritis of the hip, transient osteoporosis, transient osteoporosis of the hip, trigeminal neuralgia, tumor induced hypocalcemia, or vertebral crush fracture.

Embodiment 21

The method of embodiment 20, wherein the disease or condition comprises osteoporosis.

Embodiment 22

The method of embodiment 20, wherein the disease or condition comprises inflammatory pain.

Embodiment 23

The method of embodiment 20, wherein the disease or condition comprises arthritis.

Embodiment 24

The method of embodiment 20, wherein the disease or condition comprises multiple myeloma.

Embodiment 25

The method of embodiment 20, wherein the disease or condition comprises Paget's disease.

Example 1

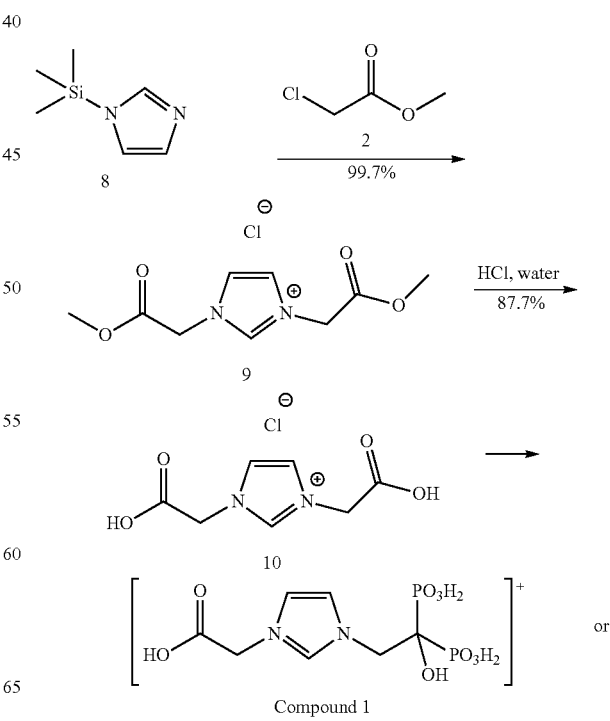

-continued

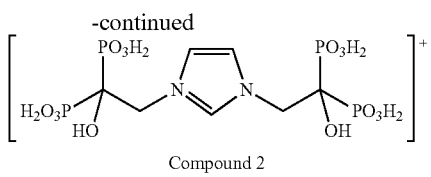

Compound 2

1,3-Bis(2-methoxy-2-oxoethyl)-1H-imidazol-3-ium chloride (9)

Methyl chloroacetate (2; 29.8 mL, 338.6 mmol, 2.0 eq) was added drop-wise to 1-(trimethylsilyl)-1H-imidazole (8; 25.0 mL, 169.3 mmol). The mixture was heated at 60° C. for 24 hours. The mixture was cooled to room temperature, washed with $Et_2O$ (3×500 mL) and dried in vacuo yielding 9 (41.97 g, 168.8 mmol, 99.7%) as a white solid.

1,3-Bis(carboxymethyl)1H-imidazol-3-ium chloride (10)

To 1,3-bis(2-methoxy-2-oxoethyl)-1H-imidazol-3-ium chloride (9; 41.00 g, 164.88 mmol, 1 eq.) was added 37% aq. HCl (30.03 mL, 362.74 mmol, 2.2 eq.). The mixture was stirred under reflux for 0.5 hour. The mixture was concentrated and the remaining solid was washed with acetone (2×200 mL) and $Et_2O$ (3×200 mL). Drying in in vacuo gave 10 (31.89 g, 144.55 mmol, 87.7%) as a white solid.

Compound 1:

Compound 10 is reacted with an equimolar amount of phosphorous acid, followed by an equimolar amount of phosphorous trichloride, and an excess of water to form Compound 1, which is precipitated from ethanol.

Compound 2:

1,3-Bis(carboxymethyl)-1H-imidazol-3-ium chloride (10, 2.00 g, 9 mmol, 1.0 eq) and $H_3PO_3$ (7.37 g, 90 mmol, 10 eq) were dissolved in toluene (10 mL) and heated to 70° C. The reaction mixture was stirred at this temperature for 20 min before $PCl_3$ (16 mL, 180 mmol, 20 eq) was added within 30 min. The reaction mixture was then heated to 95° C. and stirred at this temperature for 2 h. Then, aq. HCl (30 mL, 37% HCl and 5 mL $H_2O$) was added. The reaction mixture was heated to 100° C. and stirred at this temperature for 7 h, for 2 d stirred at room temperature and then filtered. The filtrate was cooled in an ice bath and added within 45 min to absolute EtOH (90 mL). The resulting turbid solution was stirred for 1 h at room temperature before the solid was filtered off. The filter cake (46-1) was isolated and analyzed by 2D-NMR spectroscopy and mass spectrometry (m/z=477). The filtrate was concentrated in vacuo to give residue 46-2. Five hundred mg of this residue were treated with aq. NaOH (150 mg in 3.5 mL $H_2O$) and to this was added EtOH (7 mL). After standing overnight the liquid was decanted and the resulting solid (46-M4) was analyzed NMR and mass spectrometry (m/z=477).

Unless otherwise indicated, all numbers expressing quantities of ingredients, properties such as molecular weight, reaction conditions, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A pharmaceutical dosage form comprising a compound represented by a formula:

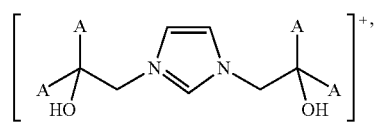

or a salt thereof;
 wherein the compound is at least 1% of the total weight of active agent in the pharmaceutical dosage form;
 wherein each A is independently an acidic functional group.

2. The pharmaceutical dosage form of claim 1, wherein each A is $CO_2H$.

3. The pharmaceutical dosage form of claim 1, wherein each A is SO₂H.

4. A method of treating a disease or condition associated with bone, cancer, or pain, comprising administering a dosage form of claim 1 to a mammal in need thereof;
wherein the disease or condition is acute pain, central pain, radio-therapy or chemo-therapy associated neuropathy, ankylosing spondylitis, arthritis, axial spondyloarthritis, a blood cancer, bone fracture, bone metastases from a solid tumor, bone metastasis, breast cancer, cancer, central multiple sclerosis pain, Charcot's foot, chronic pain, complex regional pain syndrome, diabetic peripheral neuropathy, erosive osteoarthritis, excessive bone resorption, fibrous dysplasia, giant cell tumor of bone, HIV-associated neuropathy, hypercalcemia of malignancy, inflammatory pain, juvenile rheumatoid arthritis, leukemia, low back pain, lumbar nerve root compression, lumbosacral pain, lung cancer, metastatic bone cancer, a monoradiculopathy, multiple myeloma, musculoskeletal pain, a neuropathic arthropathy, neuropathic pain, non-articular rheumatism, osteoarthritis, osteogenesis imperfecta, osteoporosis, Paget's disease of bone, a peri-articular disorder, phantom limb pain, post-herpetic neuralgia, postoperative pain, post-stroke pain, prostate cancer, rheumatoid arthritis, SAPHO syndrome, a sero-negative or non-rheumatoid arthropathy, a solid tumor or cancer, spinal cord injury, systemic lupus erythematosus, transient osteoporosis, transient osteoporosis of the hip, trigeminal neuralgia, tumor induced hypocalcemia, or vertebral crush fracture, or a combination thereof.

5. The method of claim 4, wherein the mammal is a human being.

6. The method of claim 4, wherein the disease or condition is an inflammatory pain, arthritis, osteoporosis, multiple myeloma, or bone metastasis from solid tumors.

7. A pharmaceutical dosage form comprising:

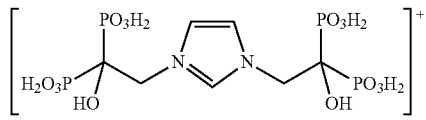

(Compound 2), or a salt thereof, in an amount that is at least 1% of the total weight of all therapeutically active agents in the pharmaceutical dosage form.

8. The pharmaceutical dosage form of claim 7, wherein zoledronic acid is less than 95% w/w of the total amount of all therapeutically active agents present in the pharmaceutical dosage form.

9. The pharmaceutical dosage form of claim 7, wherein Compound 2, or a salt thereof, is the sole active agent present in the pharmaceutical dosage form.

10. A method of treating a disease or condition associated with bone, cancer, or pain, comprising administering the pharmaceutical dosage form of claim 7 to a mammal in need thereof;
wherein the disease or condition is acute pain, central pain, radio-therapy or chemo-therapy associated neuropathy, ankylosing spondylitis, arthritis, axial spondyloarthritis, a blood cancer, bone fracture, bone metastases from a solid tumor, bone metastasis, breast cancer, cancer, central multiple sclerosis pain, Charcot's foot, chronic pain, complex regional pain syndrome, diabetic peripheral neuropathy, erosive osteoarthritis, excessive bone resorption, fibrous dysplasia, giant cell tumor of bone, HIV-associated neuropathy, hypercalcemia of malignancy, inflammatory pain, juvenile rheumatoid arthritis, leukemia, low back pain, lumbar nerve root compression, lumbosacral pain, lung cancer, metastatic bone cancer, a monoradiculopathy, multiple myeloma, musculoskeletal pain, a neuropathic arthropathy, neuropathic pain, non-articular rheumatism, osteoarthritis, osteogenesis imperfecta, osteoporosis, Paget's disease of bone, a peri-articular disorder, phantom limb pain, post-herpetic neuralgia, postoperative pain, post-stroke pain, prostate cancer, rheumatoid arthritis, SAPHO syndrome, a sero-negative or non-rheumatoid arthropathy, a solid tumor or cancer, spinal cord injury, systemic lupus erythematosus, transient osteoporosis, transient osteoporosis of the hip, trigeminal neuralgia, tumor induced hypocalcemia, or vertebral crush fracture, or a combination thereof.

11. The method of claim 10, wherein the mammal is a human being.

12. The method of claim 10, wherein the disease or condition comprises osteoporosis.

13. The method of claim 10, wherein the disease or condition comprises inflammatory pain.

14. The method of claim 10, wherein the disease or condition comprises arthritis.

15. The method of claim 10, wherein the disease or condition comprises multiple myeloma.

16. The method of claim 10, wherein the disease or condition comprises Paget's disease.

17. The pharmaceutical dosage form of claim 7, which is an oral dosage form.

18. The method of claim 10, wherein the dosage form is administered orally.

* * * * *

UNITED STATES PATENT AND TRADEMARK OFFICE
CERTIFICATE OF CORRECTION

PATENT NO. : 8,901,162 B1
APPLICATION NO. : 14/288713
DATED : December 2, 2014
INVENTOR(S) : Herriot Tabuteau It is certified that error appears in the above-identified patent and that said Letters Patent is hereby corrected as shown below:

In the specification:

In column 1, line 22, "imidizolium" should read --imidazolium--

In column 3, line 26, "arthropaties" should read --arthropathies--

In column 3, line 32, "75 years old," should read --75 years,--

In column 3, line 39, "affects, a knee," should read --affects a knee--

In column 9, line 67, "arthropaties," should read --arthropathies--

Signed and Sealed this
Fourteenth Day of June, 2016

Michelle K. Lee
*Director of the United States Patent and Trademark Office*